United States Patent
Singh et al.

(10) Patent No.: US 7,597,818 B2
(45) Date of Patent: Oct. 6, 2009

(54) AZEOTROPE-LIKE COMPOSITIONS OF TETRAFLUOROPROPENES AND BROMOFLUOROPROPENES

(75) Inventors: Rajiv R Singh, Getzville, NY (US); David P Wilson, East Amherst, NY (US); Ian Shankland, Randolph, NJ (US); Hang T Pham, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 138 days.

(21) Appl. No.: 11/711,225

(22) Filed: Feb. 27, 2007

(65) Prior Publication Data

US 2008/0203349 A1 Aug. 28, 2008

(51) Int. Cl.
C09K 5/04 (2006.01)
C08J 9/228 (2006.01)
B08B 3/04 (2006.01)

(52) U.S. Cl. ............................ 252/67; 252/68; 252/69; 252/2; 252/364; 521/98; 521/909; 521/910; 134/42; 264/416; 264/DIG. 5

(58) Field of Classification Search ............... 252/67, 252/68, 69, 364, 2; 521/909, 910, 98; 264/416, 264/DIG. 5; 134/42
See application file for complete search history.

(56) References Cited

U.S. PATENT DOCUMENTS

| 5,900,185 | A | 5/1999 | Tapscott | 252/67 |
|---|---|---|---|---|
| 5,993,682 | A | 11/1999 | Tapscott et al. | 252/8 |
| 6,031,011 | A | 2/2000 | Tapscott | 521/98 |
| 6,300,378 | B1 | 10/2001 | Tapscott | 514/743 |
| 7,223,351 | B2 * | 5/2007 | Sharma et al. | 252/2 |
| 2004/0217322 | A1* | 11/2004 | Sharma et al. | 252/2 |
| 2006/0266976 | A1 | 11/2006 | Minor et al. | |
| 2007/0098646 | A1* | 5/2007 | Nappa et al. | 424/45 |
| 2007/0100009 | A1* | 5/2007 | Creazzo et al. | 521/98 |
| 2007/0100010 | A1* | 5/2007 | Creazzo et al. | 521/98 |
| 2007/0100011 | A1* | 5/2007 | Creazzo et al. | 521/98 |
| 2007/0102021 | A1* | 5/2007 | Nappa et al. | 134/2 |
| 2007/0105738 | A1* | 5/2007 | Nappa et al. | 510/245 |

FOREIGN PATENT DOCUMENTS

| WO | 2004094002 | 11/2004 |
|---|---|---|
| WO | 2007002625 | 1/2007 |
| WO | 2008054780 | 5/2008 |

OTHER PUBLICATIONS

CAS reg. No. 754-12-1, Nov. 1984.*
CAS reg. No. 1645-83-6, Nov. 1984.*
CAS reg. No. 431-49-2, Nov. 1984.*

* cited by examiner

*Primary Examiner*—Douglas Mc Ginty
(74) *Attorney, Agent, or Firm*—Colleen D. Szuch

(57) ABSTRACT

Mixtures of tetrafluoropropenes with bromofluoropropenes provide compositions that have boiling points within an acceptable range, have good chemical stability, low GWP and are essentially non-flammable.

24 Claims, No Drawings

AZEOTROPE-LIKE COMPOSITIONS OF TETRAFLUOROPROPENES AND BROMOFLUOROPROPENES

FIELD OF INVENTION

The present invention provides compositions, particularly azeotrope-like compositions, of fluoropropenes and bromofluoropropenes having both low global warming potential (GWP) and non-flammability, and to uses of such compositions.

BACKGROUND TO THE INVENTION

Concern over human impact on climate change prompted a 1997 United Nations conference in Kyoto, Japan. The resulting Kyoto Protocol seeks to stabilize greenhouse gases in the atmosphere "at a level that would prevent dangerous anthropogenic interference with the climate system."

Perfluorocarbon compounds (PFC's), hydrofluorocarbon compounds (HFC's), chlorofluorocarbons (CFC's), hydrochlorofluorocarbon compounds (HCFC's), and their like, have been widely used in a broad variety of industrial, commercial, consumer and public use applications and uses. Recently, concern has increased about potential damage to the earth's atmosphere and climate, and certain perfluorocarbon compounds (PFC's), hydrofluorocarbon compounds (HFC's), chlorofluorocarbons (CFC's), hydrochlorofluorocarbon compounds (HCFC's), and their like, have been identified as particularly problematic in this regard, at least in part because of the greenhouse gas effect and relatively high global warming potentials (GWP) associated with those compounds. In view of the relatively high GWP of these compounds there has been a vigorous search for alternative compounds of lower GWP to replace these compounds of higher GWP in those use, application and compositions to be used in such applications and uses.

The entry into force of the Kyoto Protocol on Feb. 16, 2005 has accelerated the need for elimination or greatly reducing the use of GWP compositions. Thus, there is a continual search for new fluorocarbon and hydrofluorocarbon compositions for use, especially in air conditioning and refrigeration uses, so as to reduce global warming and for lessening possible depletion of the ozone layer. There is particularly a need for such new compositions that are essentially non-flammable and essentially non-toxic, and that do not have a deleterious effect on the atmosphere. Hydrofluoroolefin (HFO) propenes have been proposed as candidates for such compositions. However, these HFO propenes are flammable by ASHRAE (American Society of Heating, Refrigerating and Air-Conditioning Engineers, Inc) standards.

Additionally, since the commercial introduction of R-134a (1,1,1,2-tetrafluoroethane) and other similar HFCs, compressors have been engineered to take advantage of their excellent chemical stability. Thus, new low GWP compositions designed for use as refrigerants should preferably have similar stability, as well as being non-flammable and have a boiling point within a reasonable range so that the pressures should be similar to refrigerants now in use. While a number of compositions and mixtures have been proposed as a solution to this problem of developing suitable low GWP working compositions there has not yet been developed a composition or mixture of compositions that has an acceptable combination of boiling point, chemical stability, low GWP and non-flammability. For example, carbon dioxide is an example of a refrigerant that is stable and has low GWP, but whose pressures are significantly higher than refrigerants now in use. This deficiency generates significant problems in attempting to implement its use in the refrigeration industry. Thus, there is still a significant need to develop a composition or mixture of compositions that has an acceptable combination of boiling point, chemical stability, low GWP and non-flammability. The use of single component fluids or azeotropic mixtures, which do not fractionate on boiling and evaporation, is desirable. However, the identification of new, environmentally-safe, non-fractionating mixtures is complicated due to the fact that azeotrope formation is not readily predictable.

The industry is continually seeking new fluorocarbon based mixtures that offer alternatives, and are considered environmentally safer substitutes for CFCs and HCFCs. Of particular interest are mixtures containing both fluoroolefins and other fluorinated compounds, both of low ozone depletion potentials and low global warming potentials. Such mixtures are the subject of this invention.

SUMMARY OF THE INVENTION

The present inventors have discovered that azeotrope-like mixtures of tetrafluoropropenes and bromofluoropropenes are essentially non-flammable and have low GWP, and additionally possess appropriate boiling points and acceptably good chemical stability. In accordance with the present invention the inventors have discovered azeotrope-like mixtures of tetrafluoropropenes and bromofluoropropenes will provide compositions having low GWP and are essentially non-flammable. The compositions also possess boiling points within an acceptable range and have acceptable chemical stability. Preferred among such compositions are those of tetra fluoropropenes, such as 1,1,1,2-tetrafluoropropene (HFO-1234yf) or 1,1,1,3-tetrafluoropropene (HFO-1234ze) or mixtures of such tetrafluoropropenes, with bromofluoropropenes such as 3,3,1,1,1-pentafluoro-2-bromopropene (BFO-1215B1). The inventors have discovered that azeotrope-like compositions of tetrafluoropropenes and bromofluoropropenes can be formed. Thus, this invention also provides for methods of forming such azeotope-like compositions by combining tetrafluoropropenes and bromofluoropropenes in amounts effective to produce such azeotrope-like compositions. Such compositions are non-flammable according to ASHRAE Standard 34 (2004). The azeotrope-like compositions of this invention are useful for a wide variety of purposes, including but not limited to, use in refrigeration, air conditioning, heat pumps, propellants foaming or blowing agents, solvents and cleaning agents, and aerosols. The azeotrope-like compositions are especially useful as refrigerant and air conditioning compositions.

The azeotrope-like compositions of this invention can comprise any suitable tetrafluoropropene(s) and suitable bromofluoropropenes. The suitable tetrafluoropropenes include, but are not limited to 1,1,1,2-tetrafluoropropene (HFO-1234yf) or 1,1,1,3-tetrafluoropropene (HFO-1234ze) or mixtures of such tetrafluoropropenes. The suitable bromofluoropropenes include, but are not limited to, 1-bromo-1,1-difluoro-2-propene ($CH_2$=$CHCF_2Br$); 2-bromo-1,1,1-trifluoro-2-propene ($CH_2$=$CBrCF_3$); 1-bromo-3,3,3-trifluoro-1-propene (BrCH=$CHCF_3$); 3-bromo-1,1,3,3-tetrafluoro-1-propene ($CF_2$=$CHCF_2Br$); 2,3-dibromo-3,3-difluoro-1-propene ($CH_2$=$CBrCBrF_2$); 1,2-dibromo-3,3,3-trifluoro-1-propene (BrCH=$CBrCF_3$); 2-bromo-1,1,1-trifluoro-2-propene ($CF_3$ CHBr=$CH_2$); and 3,3,1,1,1- pentafluoro-2-bromopropene ($CF_3CBr=CF_2$) and is 3,3,1,1,1-pentafluoro-2-bromopropene (BFO-1215B1)

DESCRIPTION OF PREFERRED EMBODIMENTS

This invention provides low GWP, essentially non-flammable, chemically stable, compositions having an acceptable boiling point, with the composition being azeotropic-like, constant boiling compositions. While tetrafluoropropenes, e.g., HFO-1234ze, are flammable, the compositions of this invention containing such tetrafluoropropenes are non-flammable.

As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant-boiling and cannot be separated during a phase change.

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling". As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

It is well-recognized in the art that it is not possible to predict the formation of azeotropes. (See, for example, U.S. Pat. No. 5,648,017 (column 3, lines 64-65) and U.S. Pat. No. 5,182,040 (column 3, lines 62-63), both of which are incorporated herein by reference). Applicants have discovered unexpectedly that tetrafluoropropenes and bromofluoropropenes, and particularly, HFO-1234yf or HFO-1234ze and BFO-1215B1 form azeotrope-like compositions.

According to certain preferred embodiments, the azeotrope-like compositions of the present invention comprise, and preferably consist essentially of, effective amounts of tetrafluoropropenes (HFO-1234) and bromofluoropropenes (BFOs). The term "effective amounts" as used herein refers to the amount of each component which upon combination with the other component, results in the formation of an azeotrope-like composition of the present invention. Preferably, the compositions of this invention comprise any suitable amounts of tetrafluoropropene(s) and bromofluoropropenes such that the resulting compositions have a low GWP, are chemically stable, and constant boiling or azeotrope-like. It is further preferred that the amount of the bromofluoropropene be such as to render the composition essentially non-flammable and having a low GWP, an acceptable boiling point and acceptable chemical stability can be employed in the compositions of this invention. Such compositions generally will comprise, and preferably consist essentially of, from less than about 100% to about 30%, preferably from about 99% to about 40%, more preferably from about 99% to about 50%, and still more preferably from about 99% to about 60%, by weight of tetrafluoropropene(s) and from about more than 0% to about 70%, preferably from about 1% to about 60%, more preferably from about 1% to about 50%, and still more preferably from about 1% to about 40%, by weight of bromofluoropropene, wherein the weight percents are based on the total weight of these two components. The preferred tetrafluoropropene(s) is/are 1,1,1,2-tetrafluoropropene, 1,1,1,3-tetrafluoropropenes and mixtures thereof and the bromofluoropropene is preferably 3,3,1,1,1-pentafluoro-2-bromopropene. When mixtures of tetrafluoropropenes are employed HFO-1234ze (trans- and cis-1,1,1,3-tetrafluoropropene and more particularly trans-1,1,1,3-tetrafluoropropene) will be the minor component to the main tetrafluoropropene HFO-1234yf (1,1,1,2-tetrafluoropropene). The amount of HFO-1234ze is such that the azeotropic nature of the composition is not affected. Generally the maximum amount of HFO-1234ze in the mixture of tetrafluoropropenes will be about 5 wt %, more preferably about 3 wt %, and even more preferably no more than about 1 wt %, with HFO-1234yf being the remaining wt % of the tetrafluoropropene mixture.

The boiling points of the compositions at a pressure of about 14.42 psia will vary with the amount and type of tetrafluoropropene component in the composition. For compositions containing HFO-1234yf, the boiling point range of the compositions can be expected to be from about −29.2° C. to about −20° C. For compositions containing HFO-1234ze, the boiling point range of the compositions can be expected to be from about −18.6° C. to about −10° C. The compositions described herein preferably have a boiling point of from about −10° C. to about −29.2° C. at a pressure of about 14.42 psia. The compositions of this invention have a low GWP, generally a GWP of less than about 20.

The azeotrope-like compositions of the present invention can be produced by combining effective amounts of tetrafluoropropenes and bromofluoropropenes. Any of a wide variety of methods known in the art for combining two or more components to form a composition can be adapted for use in the present methods to produce an azeotrope-like composition. For example, tetrafluoropropenes and bromofluoropropenes, such as for example, HFO-1234yf and BFO-1215B1, can be mixed, blended, or otherwise contacted by hand and/or by machine, as part of a batch or continuous reaction and/or process, or via combinations of two or more such steps. In light of the disclosure herein, those of skill in the art will be readily able to prepare azeotrope-like compositions according to the present invention without undue experimentation.

The compositions of the present invention may further include any of a variety of optional additives including stabilizers, metal passivators, corrosion inhibitors, and the like.

According to certain embodiments, the compositions of the present invention further comprise a stabilizer. Any of a variety of compounds suitable for stabilizing a composition of the present invention may be used. Examples of certain preferred stabilizers include stabilizer compositions comprising at least one phenol composition and at least one epoxide selected from the group consisting of aromatic epoxides, alkyl epoxides, alkenyl epoxides, and combinations of two or more thereof.

Any of a variety of phenol compounds is suitable for use in the present compositions. As used herein the term "phenol compound" refers generally to any substituted or unsubstituted phenol. Examples of suitable phenol compounds include phenols comprising one or more substituted or unsubstituted cyclic, straight-chain, or branched aliphatic substituent group, such as, alkylated monophenols including: 2,6-di-tert-butyl-4-methylphenol; 2,6-di-tert-butyl-4-ethylphenol; 2,4-dimethyl-6-tert-butylphenol; tocopherol; and the like, hydroquinone and alkylated hydroquinones including: t-butyl hydroquinone; other derivatives of hydroquinone; and the like, hydroxylated thiodiphenyl ethers including: 4,4'-thiobis(2-methyl-6-tert-butylphenol); 4,4'-thiobis(3-methyl-6-tert-butylphenol); 2,2'-thiobis(4-methyl-6-tert-butylphenol; and the like, alkylidene-bisphenols including: 4,4'-methylenebis(2,6-di-tert-butylphenol); 4,4'-bis(2,6-di-tert-butylphenol; derivatives of 2,2- or 4,4-biphenyldiols; 2,2'-methylenebis(4-ethyl-6-tert-butylphenol); 2,2'-methylenebis(4-methyl-6-tert-butylphenol); 4,4,-butylidenebis(3-methyl-6-tert-butylphenol); 4,4,-isopropylidenebis(2-,6-di-tert-butylphenol); 2,2'-methylenebis(4-methyl-6-nonylphenol); 2,2'-isobutylidenebis(4,6-dimethylphenol); 2,2'-methylenebis(4-methyl-6-cyclohexylphenol), 2,2- or 4,4-biphenyldiols including 2,2'-methylenebis(4-ethyl-6-tertbutylphenol), butylated hydroxy toluene (BHT), bisphenols comprising heteroatoms including: 2,6-di-tert-.alpha.-dimethylamino-p-cresol; 4,4-thiobis(6-tert-butyl-m-cresol); and the like; acylaminophenols; 2,6-di-tert-butyl-4(N,N'-dimethylaminomethylphenol); sulfides including: bis(3-methyl-4-hydroxy-5-tert-butylbenzyl)sulfide; bis(3,5-di-tert-butyl-4-hydroxybenzyl) sulfide; and the like; as well as, phenolic UV absorb and light stabilizers. Certain preferred phenols include alkylated monophenols such as tocopherol, BHT, hydroquinones, and the like. Certain particularly preferred phenols include tocopherol, and the like. Most phenols are commercially available. A single phenol compound and/or mixtures of two or more phenols may be used in the present compositions. Any of a variety of epoxides is suitable for use in the compositions of the present invention. A single aromatic epoxide and/or mixtures of two or more aromatic epoxides may be used in the present compositions.

Examples of suitable aromatic epoxides include those defined by the formula (I) below:

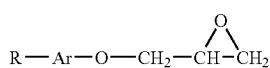
(I)

wherein: R is hydrogen, hydroxyl, alkyl, fluoroalkyl, aryl, fluoroaryl, or

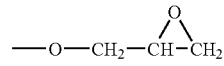

and Ar is a substituted or unsubstituted phenylene or napthylene moiety. Certain preferred aromatic epoxides of Formula I include those wherein Ar is phenylene or phenylene substituted with one or more substituents including alkyls, alkenyls, alkynyls, aryls, alkylaryls, halogens, halogenated alkyls, halogenated alkenyls, halogenated alkynyls, halogenated aryls, halogenated arylalkyls, hydroxyls, heteroatom moieties, and the like. Examples of suitable compounds of Formula I wherein Ar is an unsubstituted or substituted phenylene include butylphenylglycidyl ether; pentylphenylglycidyl ether; hexylphenylglycidyl ether; heptylphenylglycidyl ether; octylphenylglycidyl ether; nonylphenylglycidyl ether; decylphenylglycidyl ether; glycidyl methyl phenyl ether; 1,4-diglycidyl phenyl diether; 4-methoxyphenyl glycidyl ether; derivatives thereof; and the like.

Certain other preferred aromatic epoxides of Formula I include those wherein Ar is napthylene or napthylene substituted with one or more substituents including alkyls, alkenyls, alkynyls, aryls, alkylaryls, halogens, halogenated alkyls, halogenated alkenyls, halogenated alkynyls, halogenated aryls, halogenated arylalkyls, hydroxyls, heteroatom moieties, and the like. Examples of suitable compounds of Formula I wherein Ar is an unsubstituted or substituted napthylene include naphthyl glycidyl ether; 1,4-diglycidyl naphthyl diether; derivatives thereof; and the like.

Examples of other suitable aromatic epoxides include bisoxiranes, such as, 2,2'[[[5-heptadecafluorooctyl]1,3-phenylene]bis[[2,2,2trifluoromethyl]ethylidene]oxymethylene] bisoxirane, and the like.

In certain preferred embodiments, the aromatic epoxides for use in the present invention comprise an epoxide of Formula I wherein Ar is phenylene, substituted phenylene, napthylene, or substituted napthylene. More preferably, the aromatic epoxides comprise an epoxide of Formula I wherein Ar is phenylene or substituted phenylene. Examples of certain more preferred aromatic epoxides include butylphenyl glycidyl ether, and the like.

Any of a variety of alkyl and/or alkenyl epoxides is suitable for use in the present compositions. Examples of suitable alkyl and alkenyl epoxides include those of Formula II:

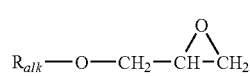
(II)

wherein $R_{alk}$ is a substituted or unsubstituted alkyl or alkenyl group. Certain preferred epoxides of Formula II comprise alkyl epoxide compounds wherein $R_{alk}$ is an alkyl group having from about 1 to about 10 carbon atoms, more preferably from about 1 to about 6 carbon atoms, and wherein the alkyl may be unsubstituted or further substituted with one or more substituents including alkyls, alkenyls, alkynyls, aryls, alkylaryls, halogens, halogenated alkyls, halogenated alkenyls, halogenated alkynyls, halogenated aryls, halogenated arylalkyls, hydroxyls, heteroatom moieties, and the like. Examples of such preferred alkyl epoxides of Formula II include n-butyl glycidyl ether, isobutyl glycidyl ether, hexanediol diglycidyl ether, and the like, as well as, fluorinated and perfluorinated alkyl epoxides, and the like. Certain more preferred alkyl epoxides comprise hexanediol diglycidyl ether, and the like.

Certain other preferred epoxides of Formula II comprise alkenyl epoxide compounds wherein $R_{alk}$ is an alkenyl group having from about 1 to about 10 carbon atoms, more preferably from about 1 to about 6 carbon atoms, and wherein the alkenyl may be unsubstituted or further substituted with one or more substituents including alkyls, alkenyls, alkynyls, aryls, alkylaryls, halogens, halogenated alkyls, halogenated alkenyls, halogenated alkynyls, halogenated aryls, halogenated arylalkyls, hydroxyls, heteroatom moieties, and the like. Examples of such preferred alkenyl epoxides of Formula II include allyl glycidyl ether, fluorinated and perfluorinated alkenyl epoxides, and the like. More preferred alkenyl epoxides include allyl glycidyl ether, and the like. A single alkyl epoxide or alkenyl epoxide and/or combinations of two or more thereof may be used in the present compositions.

In certain other preferred embodiments, the alkyl epoxide for use as an acid scavenger in the present composition comprises polypropylene glycol diglycidyl ether. Examples of polypropylene glycol diglycidyl ether suitable for use in the present invention include the ethers available commercially from SACHEM, Europe.

In addition, in certain embodiments, the epoxide for use in the present invention comprises combinations of two or more aromatic, alkyl, and/or alkenyl substituents. Such epoxides are referred to generally as "multisubstituted epoxides."

According to certain preferred embodiments, the stabilizer for use in the present invention comprises a combination of at least one phenol compound and at least one aromatic, alkyl, or alkenyl epoxide. Examples of suitable combinations include stabilizers comprising: tocopherol and allyl glycidyl ether, BHT and glycidyl butyl ether, and the like. Certain particularly preferred combinations include stabilizers comprising: tocopherol and allyl glycidyl ether, and the like.

Any suitable relative amount of the at least one phenol compound and the at least one aromatic, alkyl, or alkenyl epoxide may be used in the preferred stabilizers. For example, the weight ratio of phenol compound(s) to aromatic or fluorinated alkyl epoxide(s) can be varied from about 1:99 to about 99:1. In certain preferred embodiments, the weight ratios of phenol compound(s) to aromatic, alkyl, alkenyl, multisubstituted, or fluorinated alkyl epoxide(s) is from about 30 to about 1, more preferably from about 7 to about 1, more preferably from about 2 to about 1, and even more preferably about 1:1.

Any suitable effective amount of stabilizer may be used in the compositions of the present invention. As used herein, the term "effective stabilizing amount" refers to an amount of stabilizer of the present invention which, when added to a composition results in a stabilized composition wherein the composition degrades more slowly and/or to a lesser degree relative to the original composition, under the same, or similar, conditions. In certain preferred embodiments, an "effective stabilizing amount" of stabilizer comprises an amount which, when added to a composition results in a stabilized composition wherein the composition degrades more slowly and/or to a lesser degree relative to the original composition under the conditions of at least one, or both, of the standards tests SAE J1662 (issued June 1993) and/or ASHRAE 97-1983R. In certain more preferred embodiments, an "effective stabilizing amount" of stabilizer comprises an amount which, when added to a composition results in a composition having a stability that is at least as good as, if not better, than the stability of a comparable composition comprising dichlorodifluoromethane (R-12) in mineral oil, under at least one of the standard tests SAE J1662 (issued June 1993) and/or ASHRAE 97-1983R. Certain preferred effective amounts of stabilizer for use in the present invention comprise from about 0.001 to about 10, more preferably from about 0.01 to about 5, even more preferably from about 0.3 to about 4 weight percent, and even more preferably from about 0.3 to about 1 weight percent based on the total weight of the composition of the present invention.

In certain preferred embodiments, the compositions of the present invention further comprise a lubricant. Any of a variety of conventional lubricants may be used in the compositions of the present invention. An important requirement for the lubricant is that, when in use in a refrigerant system, there must be sufficient lubricant returning to the compressor of the system such that the compressor is lubricated. Thus, suitability of a lubricant for any given system is determined partly by the refrigerant/lubricant characteristics and partly by the characteristics of the system in which it is intended to be used. Examples of suitable lubricants include mineral oil, alkyl benzenes, polyol esters, including polyalkylene glycols, PAG oil, and the like. Mineral oil, which comprises paraffin oil or naphthenic oil, is commercially available. Commercially available mineral oils include Witco LP 250 (registered trademark) from Witco, Zerol 300 (registered trademark) from Shrieve Chemical, Sunisco 3GS from Witco, and Calumet RO15 from Calumet. Commercially available alkyl benzene lubricants include Zerol 150 (registered trademark). Commercially available esters include neopentyl glycol dipelargonate which is available as Emery 2917 (registered trademark) and Hatcol 2370 (registered trademark). Other useful esters include phosphate esters, dibasic acid esters, and fluoroesters. Preferred lubricants include polyalkylene glycols and esters. Certain more preferred lubricants include polyalkylene glycols.

The present compositions have utility in a wide range of applications. For example, one embodiment of the present invention relates to a refrigerant comprising the present azeotrope-like compositions.

The refrigerant of the present invention may be used in any of a wide variety of refrigeration systems including air-conditioning, refrigeration, heat pump, HVAC systems, and the like. In certain preferred embodiments, the refrigerants of the present invention are used in refrigeration systems originally designed for use with an HFC refrigerant, such as, for example, HFC-134a. The preferred refrigerants of the present invention tend to exhibit many of the desirable characteristics of HFC-134a and other HFC refrigerants, including a GWP that is as low, or lower than that of conventional HFC refrigerants and a capacity that is as high or higher than such refrigerants. In addition, the relatively constant boiling nature of the refrigerants of the present invention makes them even more desirable than certain conventional HFCs for use as refrigerants in many applications. The refrigerant compositions of the invention may be employed for cooling an article which comprises evaporating a refrigerant of the invention in the vicinity of the article to be cooled. Likewise, the refrigerant compositions of this invention may be employed for heating an article which comprises condensing a refrigerant of the invention in the vicinity of the article to be heated.

In certain other preferred embodiments, the present refrigerants of this invention are used in refrigeration systems originally designed for use with a CFC-refrigerant. Preferred refrigerants of the present invention may be used in refrigeration systems containing a lubricant used conventionally with CFC-refrigerants, such as mineral oils, silicone oils, polyalkylene glycol oils, and the like, or may be used with other lubricants traditionally used with HFC refrigerants. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

In certain embodiments, the compositions of the present invention may be used to retrofit refrigeration systems containing HFC, HCFC, and/or CFC-refrigerants and lubricants used conventionally therewith. Preferably, the present methods involve recharging a refrigerant system that contains a refrigerant to be replaced and a lubricant comprising the steps of (a) removing the refrigerant to be replaced from the refrigeration system while retaining a substantial portion of the lubricant in said system; and (b) introducing to the system a refrigerant of the present invention. As used herein, the term "substantial portion" refers generally to a quantity of lubricant which is at least about 50% (by weight) of the quantity of lubricant contained in the refrigeration system prior to removal of the chlorine-containing refrigerant. Preferably, the substantial portion of lubricant in the system according to the present invention is a quantity of at least about 60% of the lubricant contained originally in the refrigeration system, and more preferably a quantity of at least about 70%. As used herein the term "refrigeration system" refers generally to any system or apparatus, or any part or portion of such a system or apparatus, which employs a refrigerant to provide cooling. Such refrigeration systems include, for example, air conditioners, electric refrigerators, chillers, transport refrigeration systems, commercial refrigeration systems and the like.

Any of a wide range of known methods can be used to remove refrigerants to be replaced from a refrigeration system while removing less than a major portion of the lubricant contained in the system. For example, because refrigerants are quite volatile relative to traditional hydrocarbon-based lubricants (the boiling points of refrigerants are generally less than 10° C. whereas the boiling points of mineral oils are generally more than 200° C.), in embodiments wherein the lubricant is a hydrocarbon-based lubricant, the removal step may readily be performed by pumping chlorine-containing refrigerants in the gaseous state out of a refrigeration system containing liquid state lubricants. Such removal can be achieved in any of a number of ways known in the art, including, the use of a refrigerant recovery system, such as the recovery system manufactured by Robinair of Ohio. Alternatively, a cooled, evacuated refrigerant container can be attached to the low pressure side of a refrigeration system such that the gaseous refrigerant is drawn into the evacuated container and removed. Moreover, a compressor may be attached to a refrigeration system to pump the refrigerant from the system to an evacuated container. In light of the above disclosure, those of ordinary skill in the art will be readily able to remove chlorine-containing lubricants from refrigeration systems and to provide a refrigeration system having therein a hydrocarbon-based lubricant and substantially no chlorine-containing refrigerant according to the present invention.

Any of a wide range of methods for introducing the present refrigerant compositions to a refrigeration system can be used in the present invention. For example, one method comprises attaching a refrigerant container to the low-pressure side of a refrigeration system and turning on the refrigeration system compressor to pull the refrigerant into the system. In such embodiments, the refrigerant container may be placed on a scale such that the amount of refrigerant composition entering the system can be monitored. When a desired amount of refrigerant composition has been introduced into the system, charging is stopped. Alternatively, a wide range of charging tools, known to those of skill in the art, is commercially available. Accordingly, in light of the above disclosure, those of skill in the art will be readily able to introduce the refrigerant of the present invention into refrigeration systems according to the present invention without undue experimentation.

According to certain other embodiments, the present invention provides refrigeration systems comprising a refrigerant of the present invention and methods of producing heating or cooling by condensing and/or evaporating a composition of the present invention. In certain preferred embodiments, the methods for cooling an article according to the present invention comprise condensing a refrigerant comprising an azeotrope-like composition of the present invention and thereafter evaporating said refrigerant composition in the vicinity of the article to be cooled. Certain preferred methods for heating an article comprise condensing a refrigerant composition comprising an azeotrope-like composition of the present invention in the vicinity of the article to be heated and thereafter evaporating said refrigerant composition. In light of the disclosure herein, those of skill in the art will be readily able to heat and cool articles according to the present inventions without undue experimentation.

In another embodiment, the azeotrope-like compositions of this invention may be used as propellants in sprayable compositions, either alone or in combination with known propellants. The propellant composition comprises, more preferably consists essentially of, and, even more preferably, consists of the azeotrope-like compositions of the invention. The active ingredient to be sprayed together with inert ingredients, solvents, and other materials may also be present in the sprayable mixture. Preferably, the sprayable composition is an aerosol. Suitable active materials to be sprayed include, without limitation, cosmetic materials such as deodorants, perfumes, hair sprays, cleansers, and polishing agents as well as medicinal materials such as anti-asthma and anti-halitosis medications.

Yet another embodiment of the present invention relates to a blowing agent comprising one or more azeotrope-like compositions of the invention. In other embodiments, the invention provides foamable compositions, and preferably polyurethane and polyisocyanurate foam compositions, and methods of preparing foams. In such foam embodiments, one or more of the present azeotrope-like compositions are included as a blowing agent in a foamable composition, which composition preferably includes one or more additional components capable of reacting and foaming under the proper conditions to form a foam or cellular structure, as is well known in the art. Any of the methods well known in the art, such as those described in "Polyurethanes Chemistry and Technology," Volumes I and II, Saunders and Frisch, 1962, John Wiley and Sons, New York, N.Y., which is incorporated herein by reference, may be used or adapted for use in accordance with the foam embodiments of the present invention.

In addition, according to certain embodiments, the blowing agents of the present invention are used to blow thermoplastic foams, such as polystyrene and polyethylene foams, including low-density polyethylene foams. Any of a wide range of conventional methods for blowing such thermoplastic foams can be adapted for use herein.

According to certain other preferred embodiments, the present invention provides methods for reducing the flammability of a fluid, said methods comprising adding a composition of the present invention to said fluid. The flammability associated with any of a wide range of flammable fluids may be reduced according to the present invention. For example, the flammability associated with fluids such as ethylene oxide, flammable hydrofluorocarbons and hydrocarbons, including: HFC-152a, 1,1,1-trifluoroethane (HFC-143a), difluoromethane (HFC-32), propane, hexane, octane, and the like can be reduced according to the present invention. For the purposes of the present invention, a flammable fluid may be any fluid exhibiting flammability ranges in air as measured via any standard conventional test method, such as ASTM E-681, and the like.

Any suitable amounts of a present composition may be added to reduce flammability of a fluid according to the present invention. As will be recognized by those of skill in the art, the amount added will depend, at least in part, on the degree to which the subject fluid is flammable and the degree to which it is desired to reduce the flammability thereof. In certain preferred embodiments, the amount of composition added to the flammable fluid is effective to render the resulting fluid non-flammable.

The present invention further provides methods of suppressing a flame, said methods comprising contacting a flame with a fluid comprising a composition of the present invention. Any suitable methods for contacting the flame with the present composition may be used. For example, a composition of the present invention may be sprayed, poured, and the like onto the flame, or at least a portion of the flame may be immersed in the composition. In light of the teachings herein, those of skill in the art will be readily able to adapt a variety of conventional apparatus and methods of flame suppression for use in the present invention.

Furthermore, many articles, devices and materials, particularly for use in the medical field, must be sterilized prior to use for the health and safety reasons, such as the health and safety of patients and hospital staff. The present invention provides methods of sterilizing comprising contacting the articles, devices or material to be sterilized with a compound or composition of the present invention. Such methods may be either high or low-temperature sterilization methods. In certain embodiments, high-temperature sterilization comprises exposing the articles, device or material to be sterilized to a hot fluid comprising a compound or composition of the present invention at a temperature of from about 250 to about 270° F., preferably in a substantially sealed chamber. The process can be completed usually in less than about 2 hours. However, some articles, such as plastic articles and electrical components, cannot withstand such high temperatures and require low-temperature sterilization.

Low-temperature sterilization of the present invention involves the use of a compound or composition of the present invention at a temperature of from about 100 to about 200° F. The compounds of the present invention may be combined with other common chemical sterilants, including, for example, ethylene oxide (EO), formaldehyde, hydrogen peroxide, chlorine dioxide, and ozone to form a sterilant composition of the present invention.

The low-temperature sterilization of the present invention is preferably at least a two-step process performed in a substantially sealed, preferably air tight, chamber. In the first step (the sterilization step), the articles having been cleaned and wrapped in gas permeable bags are placed in the chamber. Air is then evacuated from the chamber by pulling a vacuum and perhaps by displacing the air with steam. In certain embodiments, it is preferable to inject steam into the chamber to achieve a relative humidity that ranges preferably from about 30% to about 70%. Such humidities may maximize the sterilizing effectiveness of the sterilant which is introduced into the chamber after the desired relative humidity is achieved. After a period of time sufficient for the sterilant to permeate the wrapping and reach the interstices of the article, the sterilant and steam are evacuated from the chamber.

In the preferred second step of the process (the aeration step), the articles are aerated to remove sterilant residues. Removing such residues is particularly important in the case of toxic sterilants, although it is optional in those cases in which the substantially non-toxic compounds of the present invention are used. Typical aeration processes include air washes, continuous aeration, and a combination of the two. An air wash is a batch process and usually comprises evacuating the chamber for a relatively short period, for example, 12 minutes, and then introducing air at atmospheric pressure or higher into the chamber. This cycle is repeated any number of times until the desired removal of sterilant is achieved. Continuous aeration typically involves introducing air through an inlet at one side of the chamber and then drawing it out through an outlet on the other side of the chamber by applying a slight vacuum to the outlet. Frequently, the two approaches are combined. For example, a common approach involves performing air washes and then an aeration cycle.

Other uses of the present compositions include use as solvents, cleaning agents, and the like. Those of skill in the art will be readily able to adapt the present compositions for use in such applications without undue experimentation.

Other uses of the present azeotrope-like compositions include use as solvents, cleaning agents, and the like. Those of skill in the art will be readily able to adapt the present compositions for use in such applications without undue experimentation.

The invention is illustrated by, but not limited to, the following examples that are intended to be illustrative, but not limiting in any manner.

EXAMPLE 1

An ebulliometer consisting of vacuum jacketed tube with a condenser on top which is further equipped with a Quartz Thermometer is used. About 18 g HFO-1234yf is charged to the ebulliometer and then BFO-1215B1 is added in small, measured increments. Temperature depression is observed when BFO-1215B1 is added to HFO-1234yf, indicating a binary minimum boiling azeotrope is formed. From greater than about 0 to about 56 weight percent BFO-1215B1, the boiling point of the composition changed by about 1.2° C. or less. The binary mixtures shown in Table 1 were studied and the boiling point of the compositions changed by less than about 2° C. The compositions exhibit azeotrope and/or azeotrope-like properties over this range.

TABLE 1

| HFO-1234yf/BFO-1215B1 compositions at 14.2 psia | | |
|---|---|---|
| T (° C.) | Wt. % HFO-1234yf | Wt. % BFO-1215B1 |
| −29.386 | 100.00 | 0.00 |
| −29.540 | 99.43 | 0.57 |
| −29.737 | 98.31 | 1.69 |
| −29.756 | 97.22 | 2.78 |
| −29.760 | 95.11 | 4.89 |
| −29.677 | 93.08 | 6.92 |
| −29.501 | 87.49 | 12.51 |
| −29.389 | 81.77 | 18.23 |
| −29.309 | 74.78 | 25.22 |
| −29.173 | 68.89 | 31.11 |
| −28.800 | 55.72 | 44.28 |
| −28.578 | 44.40 | 55.60 |
| −28.317 | 38.53 | 61.47 |
| −28.264 | 34.04 | 65.96 |

EXAMPLE 2

An ASTM-E681 apparatus was used to measure the flammability of the mixtures of HFO-1234yf and BFO-1215B1. The procedure described in the ASHRAE-34 was used to judge the flammability of the mixtures at 60° C. and at 100° C. Accordingly it was found that at 60° C., the critical flammability ratio (CFR) of the mixture was 8 mol % BFO-1215B1 and 92 mol % HFO-1234yf. Similarly it was also found that at 100° C., the critical flammability ratio (CFR) of the mixture was 10 mol % BFO-1215B1 and 90 mol % HFO-1234yf Having described the invention in detail by reference to the preferred embodiments and specific examples thereof, it will be apparent that modifications and variations are possible without departing from the spirit and scope of the disclosure and claims.

The invention claimed is:

1. An azeotrope-like composition consisting essentially of about 1 to about 60 wt. % 2-bromopentafluoropropene and about 40 to about 99 wt. % of a tetrafluoropropene selected from the group consisting of 2,3,3,3-tetrafluoropropene and 1,3,3,3-tetrafluoropropene.

2. The azeotrope-like composition of claim 1 wherein said tetrafluoropropene is 2,3,3,3-tetrafluoropropene.

3. The azeotrope-like composition of claim 1 wherein said 2-bromopentafluoropropene is present in an amount of about 1 to about 50 wt. % and said 2,3,3,3-tetrafluoropropene is present in an amount of about 50 to about 99 wt. %.

4. The azeotrope-like composition of claim 1 wherein said 2-bromopentafluoropropene is present in an amount of about 1 to about 40 wt. % and said 2,3,3,3-tetrafluoropropene is present in an amount of about 60 to about 99 wt. %.

5. The azeotrope-like composition of claim 1 wherein said tetrafluoropropene is 1,3,3,3-tetrafluoropropene.

6. The azeotrope-like composition of claim 1 wherein said 2-bromopentafluoropropene is present in an amount of about 1 to about 50 wt. % and said 1,3,3,3-tetrafluoropropene is present in an amount of about 50 to about 99 wt. %.

7. The azeotrope-like composition of claim 1 wherein said 2-bromopentafluoropropene is present in an amount of about 1 to about 40 wt. % and said 1,3,3,3-tetrafluoropropene is present in an amount of about 60 to about 99 wt. %.

8. An azeotrope-like composition according to claim 1 wherein the composition meets the non-flammability standard of ASHRAE-34 (2004) and has a GWP of 10 or less.

9. An azeotrope-like composition according to claim 1 additionally consisting essentially of one or more additional components wherein the one or more additional components are selected from the group consisting of stabilizers, metal passivators, corrosion inhibitors, and lubricants.

10. A working fluid comprising an azeotrope-like composition according to claim 1 wherein said working fluid is selected from the group consisting of a refrigerant, a blowing agent, a sprayable composition, a sterilant, a propellant, a flame suppressive, and a solvent.

11. A refrigerant comprising an azeotrope-like composition of claim 1.

12. A refrigeration system comprising a refrigerant of claim 11.

13. A method for cooling an article which comprises evaporating a refrigerant of claim 11 in the vicinity of the article to be cooled.

14. A method for heating an article which comprises condensing a refrigerant of claim 11 in the vicinity of the article to be heated.

15. A sprayable composition comprising a material to be sprayed and a propellant comprising an azeotrope-like composition of claim 1.

16. A blowing agent comprising an azeotrope-like composition of claim 1.

17. A closed cell foam prepared by foaming a foamable composition in the presence of a blowing agent comprising the composition of claim 1.

18. The closed cell foam of claim 17 wherein said foamable composition comprises polyurethane, polyisocyanu rate, polystyrene, polyethylene, and mixtures thereof.

19. A method of reducing the flammability of a fluid comprising adding to said fluid a flame suppressant comprising an azeotrope-like composition of claim 1.

20. A method of suppressing a flame comprising contacting said flame with a flame suppressant comprising an azeotrope-like composition of claim 1.

21. A method of sterilizing an article, said method comprising contacting said article to be sterilized with a sterilant comprising an azeotrope-like composition of claim 1.

22. A method of forming a foam comprising adding to a foamable composition a blowing agent comprising an azeotrope-like composition of claim 1.

23. A premix of a polyol and a blowing agent wherein the blowing agent comprises an azeotrope-like composition of claim 1.

24. A method of recharging a refrigeration system that contains a refrigerant to be replaced and a lubricant comprising the steps of: (a) removing the refrigerant to be replaced from the refrigeration system while retaining a substantial portion of the lubricant in said system; and (b) introducing into the refrigeration system a refrigerant of claim 11.

* * * * *